United States Patent [19]
Scalise

[11] Patent Number: 5,788,664
[45] Date of Patent: Aug. 4, 1998

[54] SUPPOSITORY APPLICATOR

[76] Inventor: Gaspare Scalise, 890 Knollwood Rd., White Plains, N.Y. 10603-1118

[21] Appl. No.: 630,037

[22] Filed: Apr. 2, 1996

Related U.S. Application Data

[63] Continuation of Ser. No. 346,687, Nov. 30, 1994, abandoned.

[51] Int. Cl.$^6$ ............................ A61F 13/20; A61M 31/00
[52] U.S. Cl. ...................... 604/15; 604/57; 604/59; 604/60; 604/285
[58] Field of Search ........................ 604/11–18, 33, 604/36, 38, 57, 59, 60, 311, 117, 285

[56] References Cited

U.S. PATENT DOCUMENTS

| | | | |
|---|---|---|---|
| 1,127,201 | 2/1915 | Deike | 604/38 |
| 3,297,031 | 1/1967 | Bray | 604/59 |
| 3,424,258 | 1/1969 | Silver | 604/59 |
| 3,667,465 | 6/1972 | Voss . | |
| 3,831,605 | 8/1974 | Fournier . | |
| 4,060,083 | 11/1977 | Hanson | 604/59 |
| 4,361,150 | 11/1982 | Voss . | |
| 4,900,315 | 2/1990 | Lundqvist et al. . | |
| 4,990,136 | 2/1991 | Geria . | |

FOREIGN PATENT DOCUMENTS

| | | | |
|---|---|---|---|
| 0064858 | 11/1982 | European Pat. Off. | 604/60 |

*Primary Examiner*—Robert A. Clarke
*Assistant Examiner*—Dennis Ruhl
*Attorney, Agent, or Firm*—Lackenbach Siegel, Marzullo Aronson & Greenspan, P.C

[57] ABSTRACT

The present invention provides a suppository applicator for use in the application of a suppository. A suppository applicator consists of a cylinder formed with a longitudinal bore, a plunger slidingly disposed in the longitudinal bore such that the relative axial movement of the plunger in the bore causes a suppository to exit the bore. A first flange is disposed on the cylinder for providing a grip for assisting in the handling of the applicator. A second flange is disposed on the cylinder for limiting the depth of insertion of the applicator cylinder into a body cavity. A second flange is slidingly disposed on the cylinder in one embodiment. A second flange optionally consists of a first end tappered inward toward a second end. Optionally, rotation of said second flange causes translational movement of the flange along the cylinder. A means for releasably locking the second flange is provided. The means for releasably locking the second flange optionally consists of a friction fit between the cylinder and the second flange, or consists of at least one interlocking male bead, and at least one complementary female bead.

2 Claims, 3 Drawing Sheets

SUPPOSITORY APPLICATOR

This application is a continuation, of application Ser. No. 08/346,687, filed Nov. 30, 1994 now abandoned.

BACKGROUND OF THE INVENTION

This invention relates to a suppository applicator; and, more particularly, it relates to a suppository applicator for inserting a suppository into a body cavity.

Various methods exist for dispensing medication to a patient in the health care industry. By way of example, medication can be inhaled, swallowed, or inserted into a body cavity. When insertion into a body cavity is required, manual applicators to assist in the insertion of a suppository into a body cavity are utilized because they provide a safe,. reliable, and hygienic means for controlling the insertion of a suppository. Most applicators incorporate a channel and a plunger. The channel holds a suppository, and the plunger is manually or mechanically advanced to push the suppository through the channel into the cavity.

Notwithstanding the benefits to be gained by the use of these suppository applicators, there are several problems inherent in the use of these applicators. Exemplary applicators are disclosed in U.S. Pat. Nos. 3,667,465, 3,831,605, 4,361,150, 4,900,315, and 4,990,136.

A major problem with all of these applicators involves the inability to control the depth of penetration of the applicator into a body cavity. The spring loaded suppository applicator is shown in U.S. Pat. No. 4,990,136 which projects a suppository into a body cavity. However, the violent nature of the forces results in the painful use of these applicators when used for anal or vaginal insertion on humans.

Manual applicators are subject to the inexperience of the user. Consequently, the applicator may not be positioned far enough into the body cavity, e.g. past a sphincter, to allow for insertion of a suppository. Alternately, the applicator may be positioned too far into a body cavity causing insertion to be uncomfortable and running to risk of truamatizing the body cavity, e.g. the anal canal. By way of example, the applicators disclosed in U.S. Pat. Nos. 3,667,465, 3,831,605, 4,361,150, 4,900,315, and 4,990,136, all have this problem.

A secondary problem associated with devices in the art involves a lack of ability to adjust the level of insertion of the applicator to a comfortable penetration depth. By way of example, body cavities vary in size and shape by individual, e.g. some individuals may have more flesh around their buttocks. This variation in size and shape makes it desirable to be able to adjust the depth of penetration of an applicator to accommodate the specific characteristics of an individual, and to limit stop the depth of penetration. The prior art devices do not allow for a depth adjustment.

It would be highly desirable to solve the plethora of problems faced in the art and it is an object of the present invention to solve these problems. The present invention targets the thousands of users of suppositories and suppository activators in the United States and worldwide, and serves these markets by providing a suppository applicator that allows for the adjustment of penetration depths.

SUMMARY OF THE INVENTION

The present invention provides a suppository applicator for use by an individual for the application of suppositories. The applicator consists of a cylinder formed with a longitudinal bore, and a plunger slidingly disposed in the longitudinal bore such that the relative axial movement of the plunger in the longitudinal bore causes a suppository to exit the bore through a port. A first flange is disposed on the cylinder for providing a grip for assisting in the handling of the applicator. A second flange is disposed on the cylinder for limiting the depth of insertion of the cylinder into a body cavity.

An optional finger spacing is interposed between the first flange and the second flange. In one embodiment, the second flange comprises a first end that is tapered toward a second end. The second flange is optionally slidingly disposed on the cylinder. The second flange also optionally rotates so as to cause translational movement of the second flange along the cylinder.

An optional means for releasably locking the second flange is also provided. Means for releasably locking said second flange comprise a friction fit between the cylinder and the second flange in one embodiment. Means for releasably locking said second flange comprise at least one interlocking male bead, and at least one complementary female bead in another embodiment.

These and other objects of the invention will best be understood from the accompanying description, taken in conjunction with the accompanying drawings.

DETAILED DESCRIPTION OF THE INVENTION

Figure 1:
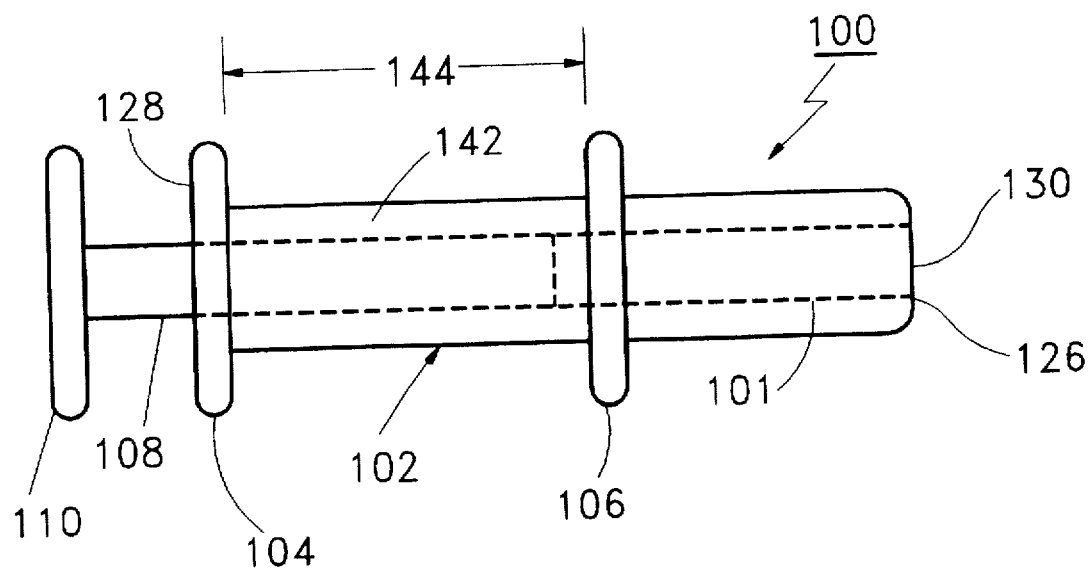
FIG. 1 is a side cross-sectional view of a suppository applicator.

FIG. 1 is a side cross-sectional view of a suppository applicator 100. Applicator 100, as viewed in FIGS. 1 and 3, comprises cylinder 102 formed with a longitudinal bore 101. Longitudinal bore 101 extends from a first end 126 of cylinder 102 to a second end 128 of cylinder 102. Plunger 108 is slidingly disposed in longitudinal bore 101 such that the relative axial movement of plunger 108 in longitudinal bore 101 causes a suppository (not pictured) to exit longitudinal bore 101 at exit port 130. Exit port 130 is disposed at first end 126.

First flange 104 is disposed on cylinder 102 at second end 128. First flange 104 provides a grip for assisting in the handling of applicator 100. As will be appreciated first flange 104 provides a surface on which a person who is manipulating the applicator can rest his fingers when applying a force to optional plunger cap 110 so that axial movement of plunger 108 can be accomplished. In a preferred embodiment, first flange 104 provides a dual finger grip in a manner analogous to a syringe so that plunger 108 can be thumb actuated to push a suppository into a body cavity.

Second flange 106 is also disposed on cylinder 102. Second flange 106 limits the depth of insertion of cylinder 102 into a body cavity (not pictured). By way of example, second flange 106 acts as a limit stop for limiting the depth of penetration of applicator 100 into an anus (not shown). Second flange 106 is fixed to cylinder 102 in one embodiment. Optionally, second flange 106 is slidingly disposed along cylinder 102.

An optional, finger spacing 144 is interposed between first flange 104 and second flange 106. As will be appreciated, finger spacing 144 facilitates the manipulation and placement of applicator 100 between the buttocks (not shown), and the insertion of a suppository (not shown) into a body cavity.

Figure 2:
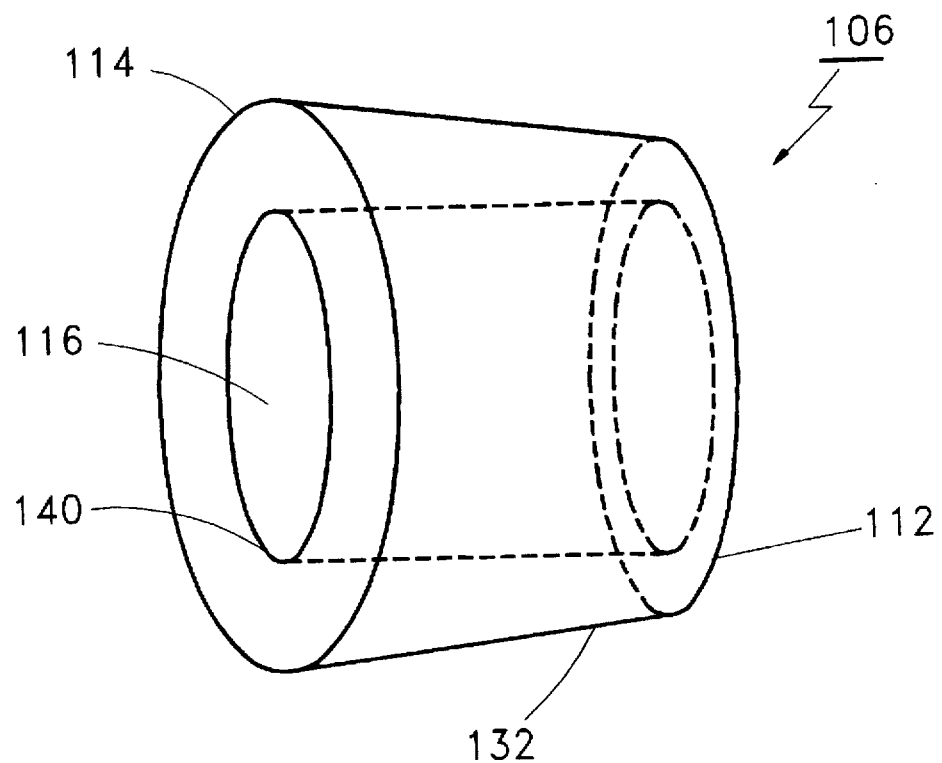
FIG. 2 is a perspective view of a tapered second flange of FIG. 1.

As illustrated in FIG. 2, second flange 106 can optionally comprise first end 112 and second end 114. Second end 114 is tapered inward to first end 112. It will be appreciated that this tapering will allow for wall 132 of second flange 106 to rest comfortably against the exterior portion of a body cavity, e.g. against an individual's buttocks.

Figure 3:
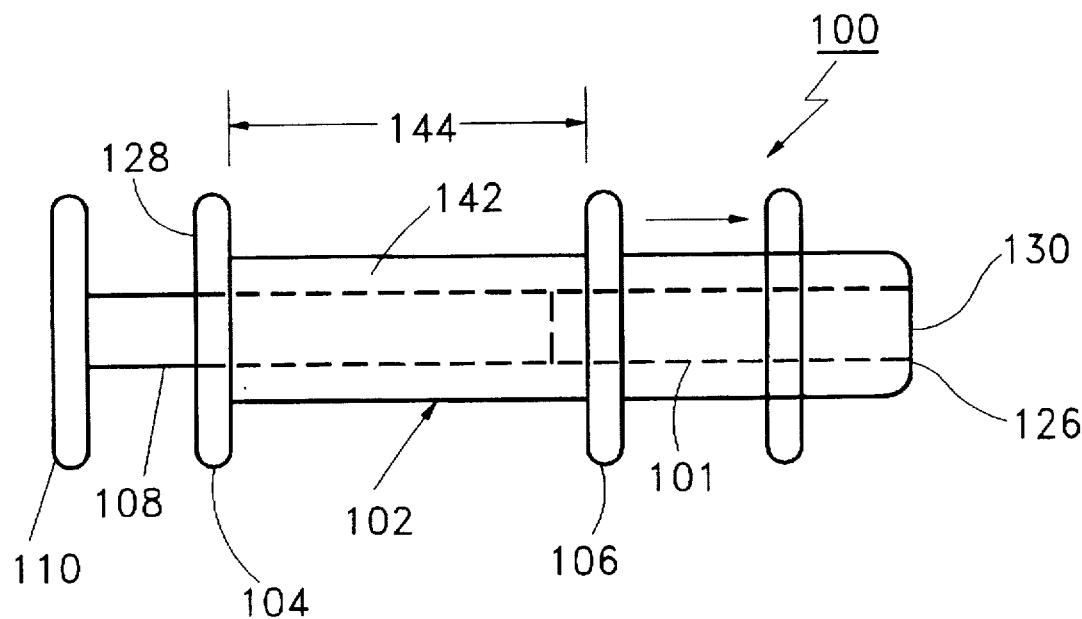
FIG. 3 is a side cross-sectional view of a suppository applicator of FIG. 1 showing the translational movement of a second flange along the cylinder.

As illustrated in FIG. 3, second flange 106 is optionally slidingly disposed on cylinder 102. Translational movement of second flange 106 along an axis of cylinder 102 allows an individual to adjust the depth of insertion of cylinder 102 into a body cavity (not pictured). As will be appreciated, adjustment of the depth of insertion increases the comfort level of the insertion of cylinder 102, and allows individuals who have varying amounts of flesh on their buttocks to adjust the depth of insertion for maximum comfort and proper penetration.

Figure 5:
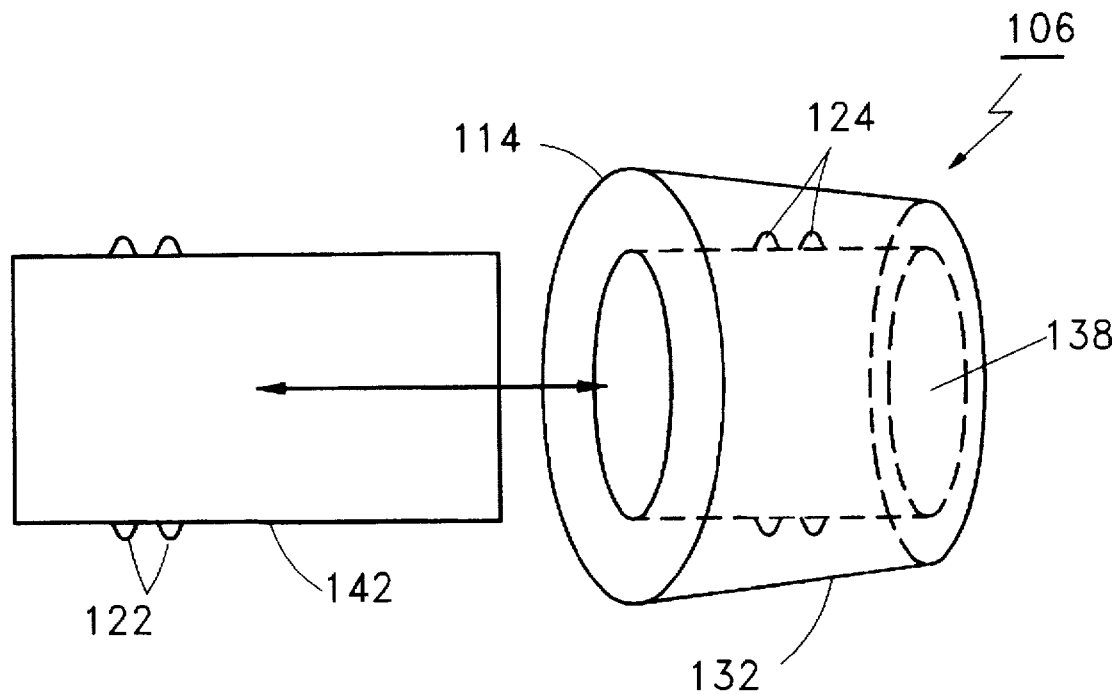
FIG. 5 is an exploded side cross-sectional view of the suppository applicator of FIG. 1 with the addition of a male and female interlocking bead assembly.
Figure 4:
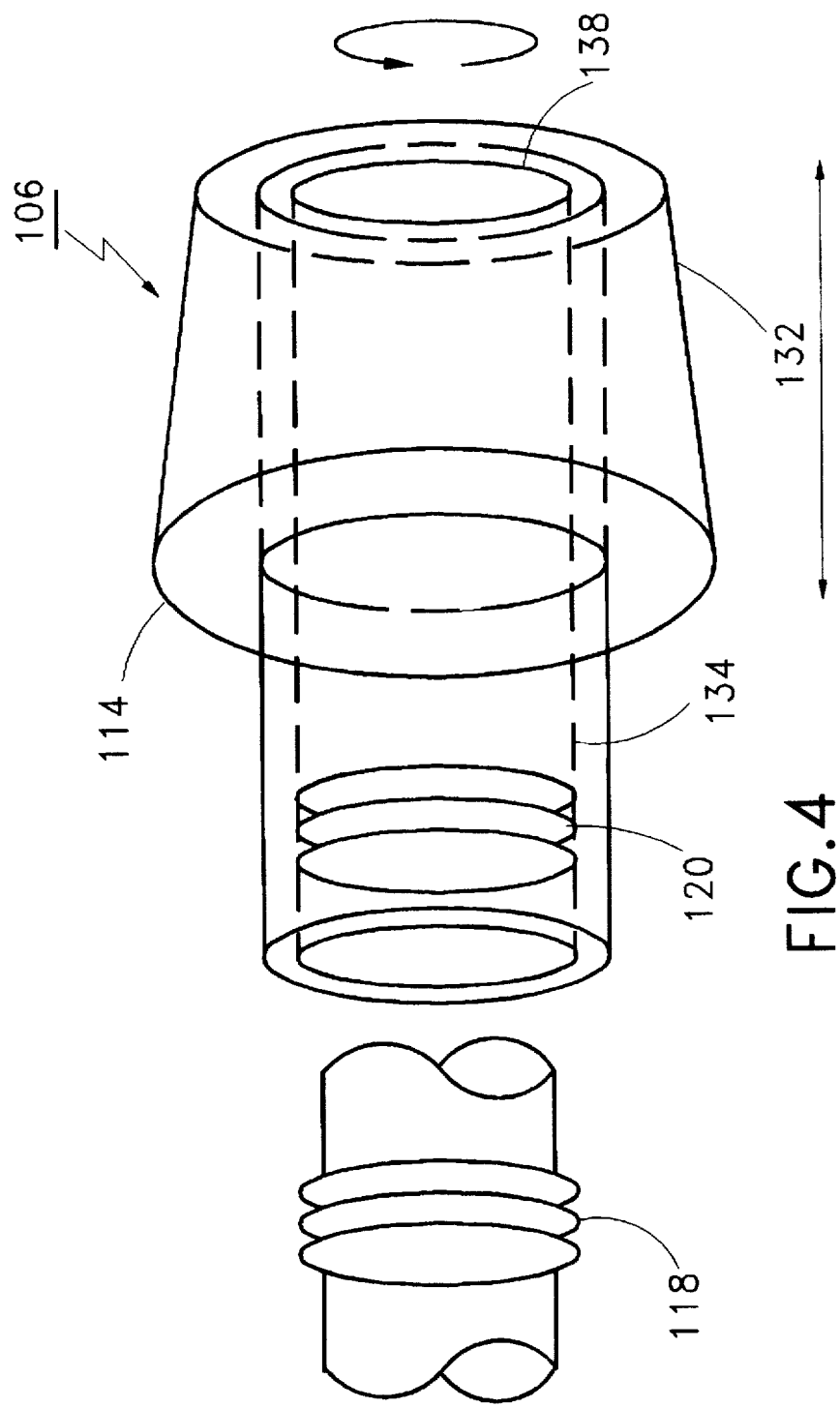
FIG. 4 is an exploded side cross-sectional view of a suppository applicator of FIG. 1 with the addition of a threaded cylinder and a complementary threaded second flange.

As illustrated in FIGS. 3, 4, and 5, applicator 100 optionally comprises means for releasably locking second flange 106. The present invention contemplates utilizing various means for releaseably locking a flange that are known in the art. Two exemplary embodiments are described herein. By way of example, a means for releasably locking second flange comprises a friction fit between cylinder 102 and second flange 106. As illustrated in FIG. 5, means for releasably locking second flange 106 optionally comprises at least one interlocking female bead 124, and cylinder 102 comprises at least one complementary male bead 122. Alternately, female bead 124 is disposed on cylinder 102 (not shown), and complementary male bead 122 is disposed on second flange 106 (not shown).

A friction fit between inner bore wall 140 of second flange 106 (FIG.2) and outer wall 142 (FIG. 1) of cylinder 102 allows for translational movement of flange 106 along cylinder 102 (FIG. 3). Alternately, translational movement of second flange 106 along cylinder 102 is accomplished by rotating second flange 106 along an axis of cylinder 102.

As illustrated in FIG. 4, translational movement of second flange 106 along cylinder 102 is accomplished by rotation of second flange 106. Second flange 106 comprises threads 120 disposed on inner cylinderical side wall portion 134 of optional second flange neck 134. Alternately, threads 120 are disposed on wall portion 138 of second flange 106. Mating threads 118 are disposed on cylinder 102. Threads 118 and threads 120 mate so as to allow rotation of second flange 106 along an axis of cylinder 102.

While only a few, preferred embodiments of the invention have been described hereinabove, those of ordinary skill in the art will recognize that the embodiment may be modified and altered without departing from the central spirit and scope of the invention. Thus, the preferred embodiment described hereinabove is to be considered in all respects as illustrative and not restrictive, the scope of the invention being indicated by the appended claims, rather than by the foregoing description, and all changes which come within the meaning and range of equivalency of the claims are intended to be embraced herein.

I claim:

1. A suppository applicator for inserting a suppository into a rectal passageway by way of the buttocks, comprising:
    (a) a cylinder having a longitudinal bore with proximal and distal openings, said cylinder having a blunt end shaped to easily enter said rectal passageway without lacerating said buttocks and said rectal passageway;
    (b) a plunger slidingly disposed in said longitudinal bore of said cylinder such that the relative axial movement of said plunger in said longitudinal bore causes a suppository, placed in said bore at said distal opening, to exit said longitudinal bore at said blunt end;
    (c) an immovable first flange disposed at said proximal opening on said cylinder, said first flange being fixedly mounted to said cylinder, and providing a finger grip for assisting in the handling and use of said applicator; and,
    (d) a movable, conical second flange threadably disposed and advanceable along a predetermined set of complementary and interlocking male and female threads provided on said cylinder and said conical second flange.
    (e) threaded means for releaseably locking said movable, conical second flange along said cylinder to prevent unintentional relocation of said movable, conical second flange along said cylinder; and
    (f) said movable, conical second flange forming a tapered cone-like element; whereby a user using said applicator may employ a dual finger grip about said immovable first flange, in a manner similar to that of gripping a syringe, and with one's thumb on said plunger safely and sanitarily push said suppository into said rectal passage way to a predetermined depth of insertion.

2. A suppository applicator for inserting a suppository into a rectal passageway by way of the buttocks, comprising:
    (a) a cylinder having a longitudinal bore with proximal and distal openings, said cylinder having a blunt end shaped to easily enter said rectal passageway without lacerating said buttocks and said rectal passageway;
    (b) a plunger slidingly disposed in said longitudinal bore such that the relative axial movement of said plunger in said longitudinal bore causes a suppository, placed in said bore at said distal opening, to exit said longitudinal bore at said blunt end;
    (c) an immovable first flange disposed at said proximal opening on said cylinder, said first flange being fixedly mounted to said cylinder, and providing a finger surface for assisting in the handling and use of said applicator;
    (d) a movable, second flange disposed on said cylinder, said movable, second flange forming a circular limit stop for limiting the depth of insertion of said cylinder into the rectal passageway, said movable, second flange being threadably disposed along said cylinder; and
    (e) means for releaseably locking said movable, second flange along said cylinder to prevent unintentional relocation of said movable, second flange along said cylinder, comprising complementary male/female interlocking elements on said cylinder and said movable, second flange; and said means for releaseably locking said movable, second flange to said cylinder comprises at least one interlocking male bead, and at least one complementary female bead which together form a threaded connection between said cylinder and said movable, second flange.

* * * * *